United States Patent
Staric et al.

(10) Patent No.: US 9,254,261 B2
(45) Date of Patent: Feb. 9, 2016

(54) STABLE QUICK DISSOLVING DOSAGE FORM COMPRISING AMOXICILLIN AND CLAVULANIC ACID

(71) Applicant: Sandoz AG, Basel (CH)

(72) Inventors: Rok Staric, Duplje (SI); Marko Oblak, Ljubljana (SI); Tanja Rozman Peterka, Ljubljana (SI); Veronika Debevec, Polhov Gradec (SI)

(73) Assignee: Sandoz AG (CH)

( * ) Notice: Subject to any disclaimer, the term of this patent is extended or adjusted under 35 U.S.C. 154(b) by 0 days.

(21) Appl. No.: 14/194,915

(22) Filed: Mar. 3, 2014

(65) Prior Publication Data

US 2015/0245995 A1    Sep. 3, 2015

(51) Int. Cl.

| | | |
|---|---|---|
| *A61K 31/43* | (2006.01) | |
| *A61K 31/424* | (2006.01) | |
| *A61K 9/00* | (2006.01) | |
| *A61K 47/10* | (2006.01) | |
| *A61K 47/32* | (2006.01) | |
| *A61K 47/02* | (2006.01) | |
| *A61K 47/12* | (2006.01) | |
| *A61K 9/20* | (2006.01) | |

(52) U.S. Cl.
CPC .............. *A61K 9/0056* (2013.01); *A61K 9/0095* (2013.01); *A61K 9/2095* (2013.01); *A61K 31/424* (2013.01); *A61K 31/43* (2013.01); *A61K 47/02* (2013.01); *A61K 47/10* (2013.01); *A61K 47/12* (2013.01); *A61K 47/32* (2013.01)

(58) Field of Classification Search
CPC ....... A61K 31/43; A61K 9/20; A61K 9/2018; A61K 9/2027; A61K 9/2036; C07D 499/00
USPC ...................... 424/464, 468; 514/192, 210.06
See application file for complete search history.

(56) References Cited

U.S. PATENT DOCUMENTS

| 6,194,001 | B1 * | 2/2001 | Gribbon et al. ................ 424/464 |
| 6,511,972 | B1 | 1/2003 | Kofler et al. |
| 7,771,745 | B2 * | 8/2010 | Wang et al. .................... 424/466 |
| 7,807,196 | B2 * | 10/2010 | Bilke et al. ..................... 424/465 |
| 2002/0006433 | A1 | 1/2002 | Davidson et al. |
| 2009/0111788 | A1 * | 4/2009 | Jain et al. ....................... 514/196 |
| 2012/0028949 | A1 | 2/2012 | Skulj et al. |

FOREIGN PATENT DOCUMENTS

| WO | WO 9835672 A1 * | 8/1998 | .............. A61K 31/43 |
| WO | WO 2005099672 A1 * | 10/2005 | ................ A61K 9/20 |
| WO | WO 2005123041 A1 * | 12/2005 | ................ A61K 9/20 |
| WO | 2006066930 A1 | 6/2006 | |

OTHER PUBLICATIONS

Remington: The Science and Practice of Pharmacy, May 2005, Lippincott Williams & Wilkins, Edition 21, pp. 891-894 and 901-904.*
Bolhuis et al., "Excipients for Direct Compaction—an Update", 2006, Pharmaceutical Development and Technology, vol. 11, pp. 111-124.*
Druffner et al., "Selecting Superdisintegrants for Orally Disintegrating Tablet Formulations", Oct. 2006, PharmTech.com Advancing Development and Manufacturing, pp. 1-4.*

* cited by examiner

*Primary Examiner* — My-Chau T Tran
(74) *Attorney, Agent, or Firm* — Luedeka Neely Group, P.C.

(57) ABSTRACT

A quick dissolving pharmaceutical formulation is disclosed. In one embodiment, the formulation includes at least the following components: (1) from about 35 to about 50 weight percent amoxicillin or a pharmaceutically acceptable salt thereof; (2) from about 2.0 to about 12 weight percent clavulanic acid or a pharmaceutically acceptable salt thereof; (3) from about 30 to about 40 weight percent mannitol; (4) from about 2 to about 7 weight percent crospovidone; (5) from about 0.5 to about 2.0 weight percent colloidal silicon dioxide; and (6) from about 2.0 to about 5.0 weight percent sodium stearyl fumarate. A method for making a quick dissolving pharmaceutical tablet is also disclosed.

20 Claims, No Drawings

STABLE QUICK DISSOLVING DOSAGE FORM COMPRISING AMOXICILLIN AND CLAVULANIC ACID

FIELD

This invention relates to the field of pharmaceutical formulation. More particularly, this invention relates to a quick dissolving pharmaceutical formulation comprising amoxicillin and clavulanic acid.

BACKGROUND

Oral suspensions of amoxicillin and clavulanic acid are commonly used for the treatment of infections in pediatric or elderly adult patients who may be unable to swallow tablets.

A problem with such oral suspension is a decrease in the chemical stability of the active ingredients, especially clavulanic acid or its salts such as potassium clavulanate. Potassium clavulanate is prone to degradation in water, particularly at higher temperatures. Accordingly, such oral suspensions are typically first provided as a dry powder which is reconstituted with water prior to treatment. Even then, the reconstituted suspension must be refrigerated for storage and used within about 10 days. Due to this instability and significant decrease in assay during this in-use period, excess amounts (or overages) of the active ingredients are required in the oral suspension in order to maintain an adequate assay of the active ingredients during the period of use. Even still, the instability of the active ingredients results in unequal dosing of the active ingredients over the course of treatment.

Moreover, oral suspension must still be refrigerated for storage, leading to more inconvenience and a loss of portability of the formulation. This in turn may lead to a decrease in patient compliance to finish the course of treatment.

Accordingly what is needed is an alternative or improved dosage form to oral suspension comprising amoxicillin and clavulanic acid. Such formulation should preferably provide improved chemical stability (especially in-use stability) of the active ingredients, accurate dosing of the active ingredients, convenient storage without the need for refrigeration, and patient friendly taste and feel.

SUMMARY OF THE INVENTION

The aforementioned and other needs are fulfilled by one or more aspects of the invention disclosed herein. The present disclosure relates to a quick dissolving pharmaceutical formulation comprising amoxicillin and clavulanic acid, a method for making a quick dissolving pharmaceutical tablet, and a method of treating a bacterial infection using such a pharmaceutical formulation.

In a first aspect, the present disclosure provides a quick dissolving pharmaceutical formulation. According to one embodiment, the pharmaceutical formulation includes at least the following components: (1) from about 35 to about 50 weight percent of a first active ingredient which comprises amoxicillin or a pharmaceutically acceptable salt thereof; (2) from about 2.0 to about 12 weight percent of a second active ingredient which comprises clavulanic acid or a pharmaceutically acceptable salt thereof; (3) from about 30 to about 40 weight percent mannitol; (4) from about 2 to about 7 weight percent crospovidone; (5) from about 0.5 to about 2.0 weight percent colloidal silicon dioxide; and (6) from about 2.0 to about 5.0 weight percent sodium stearyl fumarate.

In certain preferred embodiments, the formulation further includes silicified microcrystalline cellulose which is present in an amount less than about 10 weight percent of the pharmaceutical formulation. In some preferred embodiments, the formulation includes from about 5.0 to about 10 weight percent silicified microcrystalline cellulose.

In certain embodiments, the first active ingredient preferably comprises amoxicillin trihydrate. In some embodiments, the second active ingredient preferably comprises potassium clavulanate.

In certain embodiments, the ratio of the first active ingredient to the second active ingredient in the formulation, on a weight basis, is preferably from about 4:1 to about 14:1.

In certain embodiments, the pharmaceutical formulation is preferably a tablet which includes from about 125 to about 875 mg of the first active ingredient.

Advantageously, the present disclosure provides a pharmaceutical formulation which may be solubilized in a relatively small amount of water. In certain embodiments, the pharmaceutical formulation is preferably a tablet capable of being solubilized in water. In some embodiments, the pharmaceutical formulation is preferably a tablet capable of being solubilized in 5 milliliters of water. Moreover, the tablet may also be solubilized in other liquid food products, such as milk, juices, or yogurt.

In certain embodiments, the crospovidone is preferably pre-dried to a moisture content below 0.5 weight percent before being incorporated into the pharmaceutical formulation. In some embodiments, the silicified microcrystalline cellulose is also preferably pre-dried to a moisture content below 0.5 weight percent before being incorporated into the pharmaceutical formulation.

The present disclosure also advantageously provides a pharmaceutical formulation having improved stability or shelf life for the active ingredients used in the formulation, particularly the second active ingredient. In certain embodiments, at least 85 percent by weight of the second active ingredient remains present in the pharmaceutical formulation after being stored for 7 days at a temperature of 60 degrees C.

Further in some embodiments, at least 95 percent by weight of the second active ingredient remains present in the pharmaceutical formulation after being stored for 30 days at a temperature of 40 degrees C. and a relative humidity of about 75%.

In certain embodiments, at least 98 percent by weight of the second active ingredient remains present in the pharmaceutical formulation after being stored for 90 days at a temperature of 25 degrees C. and a relative humidity of about 60%.

In a second aspect, the present disclosure provides a method of treating a bacterial infection. According to one embodiment, the method includes administering an effective amount of a pharmaceutical formulation to a patient in need of such treatment. The pharmaceutical formulation includes at least the following components: (1) from about 35 to about 50 weight percent a first active ingredient which comprises amoxicillin or a pharmaceutically acceptable salt thereof; (2) from about 2.0 to about 12 weight percent a second active ingredient which comprises clavulanic acid or a pharmaceutically acceptable salt thereof; (3) from about 30 to about 40 weight percent mannitol; (4) from about 2 to about 7 weight percent crospovidone; (5) from about 0.5 to about 2.0 weight percent colloidal silicon dioxide; and (6) from about 2.0 to about 5.0 weight percent sodium stearyl fumarate.

In a third aspect, the present disclosure provides a method for making a quick dissolving pharmaceutical tablet. According to one embodiment, the method includes at least the steps of: (a) pre-drying crospovidone to a moisture content below 0.5 weight percent; (b) blending (i) a first active ingredient which comprises amoxicillin or a pharmaceutically acceptable salt thereof, (ii) a second active ingredient which comprises clavulanic acid or a pharmaceutically acceptable salt thereof, (iii) mannitol, (iv) crospovidone, and (v) colloidal silicon dioxide to form an intermediate mixture; (c) further blending sodium stearyl fumarate to form a final mixture; and (d) compressing the final mixture into pharmaceutical tablets.

In certain embodiments, the method also includes the step of pre-drying silicified microcrystalline cellulose to a moisture content below 0.5 weight percent. This pre-dried silicified microcrystalline cellulose is then blended into the intermediate mixture.

In certain embodiments of the method, the first active ingredient preferably comprises amoxicillin trihydrate. In some embodiments of the method, the second active ingredient preferably comprises potassium clavulanate.

In certain embodiments of the method, the tablet is preferably capable of being solubilized in water. In some embodiments of the method, the tablet is preferably capable of being solubilized in 5 milliliters of water.

A more complete appreciation of the present disclosure and its scope can be obtained from the following description of the invention.

DETAILED DESCRIPTION OF THE INVENTION

The aforementioned and other needs are fulfilled by one or more aspects of the invention disclosed herein. The present disclosure relates to a quick dissolving pharmaceutical formulation comprising amoxicillin and clavulanic acid, a method for making a quick dissolving pharmaceutical tablet, and a method of treating a bacterial infection using such a pharmaceutical formulation.

In a first aspect, the present disclosure provides a quick dissolving pharmaceutical formulation. According to one embodiment, the pharmaceutical formulation includes at least the following components: (1) from about 35 to about 50 weight percent of a first active ingredient which comprises amoxicillin or a pharmaceutically acceptable salt thereof; (2) from about 2.0 to about 12 weight percent of a second active ingredient which comprises clavulanic acid or a pharmaceutically acceptable salt thereof; (3) from about 30 to about 40 weight percent mannitol; (4) from about 2 to about 7 weight percent crospovidone; (5) from about 0.5 to about 2.0 weight percent colloidal silicon dioxide; and (6) from about 2.0 to about 5.0 weight percent sodium stearyl fumarate.

A first component of the pharmaceutical formulation is a first pharmaceutically active ingredient which comprises amoxicillin or a pharmaceutically acceptable salt thereof. The amount of the a first pharmaceutically active ingredient is generally from about 35 to about 50 weight percent of the pharmaceutical formulation. In certain embodiments, the amount of the first pharmaceutically active ingredient is more preferably from about 39 to about 47 weight percent of the pharmaceutical formulation. The overall amount of the first pharmaceutically active ingredient in the pharmaceutical formulation may in general range from about 125 mg to about 875 mg.

The first pharmaceutically active ingredient may be provided as amoxicillin or a pharmaceutically acceptable salt thereof, such as amoxicillin sodium. In certain embodiments, the first pharmaceutically active ingredient may comprise amoxicillin trihydrate. More preferably, the first pharmaceutically active ingredient is amoxicillin trihydrate.

A second component of the pharmaceutical formulation is a second pharmaceutically active ingredient which comprises clavulanic acid or a pharmaceutically acceptable salt thereof. The amount of the a second pharmaceutically active ingredient is generally from about 2.0 to about 12 weight percent of the pharmaceutical formulation. In certain embodiments, the amount of the second pharmaceutically active ingredient is more preferably from about 3.0 to about 10.0 weight percent of the pharmaceutical formulation. The overall amount of the second pharmaceutically active ingredient in the pharmaceutical formulation may in general range from about 25 mg to about 65 mg.

The second pharmaceutically active ingredient may be provided as clavulanic acid or a pharmaceutically acceptable salt thereof. Examples of such salts include potassium, sodium, lithium, calcium and magnesium salts. In certain embodiments, the second pharmaceutically active ingredient may comprise potassium clavulanate. More preferably, the second pharmaceutically active ingredient is potassium clavulanate.

The ratio, by weight of the first active ingredient to the second active ingredient in the pharmaceutical formulation preferably ranges from about 4:1 to about 14:1. Thus, exemplary tablets prepared in accordance with the present disclosure may include the following proportions of active components:

TABLE A

Proportions of First and Second Active Ingredients in Sample Inventive Tablets

| First Active (mg) | Second Active (mg) | Total Tablet Mass (mg) | Mass Ratio of 1st Active to 2nd Active |
|---|---|---|---|
| 125 | 31.25 | 320 | 4:1 |
| 150 | 10.73 | 325 | 14:1 |
| 200 | 28.5 | 470 | 7:1 |
| 250 | 62.5 | 640 | 4:1 |
| 400 | 57 | 940 | 7:1 |
| 600 | 42.9 | 1300 | 14:1 |

A third component of the pharmaceutical formulation is mannitol, which acts as an excipient in the formulation. The amount of the mannitol excipient is generally from about 30 to about 40 weight percent of the pharmaceutical formulation. In certain embodiments, the amount of the mannitol excipient is more preferably from about 33 to about 35 weight percent of the pharmaceutical formulation.

A fourth component of the pharmaceutical formulation is crospovidone, which acts as an additional excipient in the formulation. The amount of the crospovidone excipient is generally from about 2 to about 7 weight percent of the pharmaceutical formulation. In certain embodiments, the amount of the crospovidone excipient is more preferably from about 3.0 to about 4.0 weight percent of the pharmaceutical formulation.

In certain instances, this crospovidone is preferably pre-dried to a moisture content below 0.5 weight percent before being incorporated into the pharmaceutical formulation. Crospovidone excipients typically include a relatively large amount of bond water. Without being bound by theory, it is believed that pre-drying of the crospovidone excipient to remove or at least substantially reduce this bound moisture leads to improved stability of the second pharmaceutically active ingredient (clavulanic acid or a pharmaceutically acceptable salt thereof) in the final formulation.

A fifth component of the pharmaceutical formulation is colloidal silicon dioxide, which acts as a further excipient in the formulation. The amount of the colloidal silicon dioxide excipient is generally from about 0.5 to about 2.0 weight percent of the pharmaceutical formulation. In certain embodiments, the amount of the colloidal silicon dioxide excipient is more preferably from about 0.7 to about 0.8 weight percent of the pharmaceutical formulation.

A sixth component of the pharmaceutical formulation is sodium stearyl fumarate, which acts as another excipient in the formulation. The amount of the sodium stearyl fumarate excipient is generally from about 2.0 to about 5.0 weight percent of the pharmaceutical formulation. In certain embodiments, the amount of the sodium stearyl fumarate excipient is more preferably from about 2.0 to about 3.0 weight percent of the pharmaceutical formulation.

Optionally, in certain embodiments, the pharmaceutical formulation may also include a relatively small amount of silicified microcrystalline cellulose as an additional excipient. In general, it is desirable to use only a minimal amount of silicified microcrystalline cellulose in the formulation. Thus, the amount of the silicified microcrystalline cellulose excipient is generally less than about 10 weight percent of the pharmaceutical formulation. In certain embodiments, the amount of the silicified microcrystalline cellulose excipient is more preferably from about 5.0 to about 10.0 weight percent of the pharmaceutical formulation.

In certain instances, the silicified microcrystalline cellulose is preferably pre-dried to a moisture content below 0.5 weight percent before being incorporated into the pharmaceutical formulation. Silicified microcrystalline cellulose typically includes a relatively large amount of bound water. Without being bound by theory, it is believed that pre-drying of the silicified microcrystalline cellulose excipient to remove or at least substantially reduce this bound moisture leads to improved stability of the second pharmaceutically active ingredient (clavulanic acid or a pharmaceutically acceptable salt thereof) in the final formulation.

Optionally, the pharmaceutical formulation may also include additional excipients. These may include for example: (1) lubricants, such as magnesium stearate, hydrogenated vegetable oil, carnauba wax and the like; (2) antiadherents or glidants, such as talc; (3) sweeteners such as sucralose; (4) fruit or other flavoring additives; and (5) coloring additives such as iron oxide, titanium dioxide, or aluminum lake.

The quick dissolving pharmaceutical formulation of the present disclosure is preferably provided in the form of a tablet. In certain embodiments, each tablet preferably includes from about 125 to about 600 mg of the first active ingredient, i.e., amoxicillin.

Advantageously, the tablet is soluble in water, and may preferably be solubilized in a volume of 5 milliliters of water or less. Thus, when administered the tablet may be rapidly dissolved in mouth saliva or even a teaspoon of water. Moreover, the tablet may also be solubilized in other liquid food products, such as milk, juices, or yogurt. This makes the tablet of the present disclosure particularly suitable for administration to pediatric patients or to the very elderly patients—both of whom often have difficulty swallowing tablets or capsules.

Without being bound by theory, it is believed that the rapid solubility of the tablet of the present disclosure is provided by the very specific combination of excipients used in the formulation of the tablet. By combining mannitol, crospovidone, colloidal silicon dioxide, and sodium stearyl fumarate in the amounts specified in the present disclosure, the resultant tablet has been found to exhibit rapid dissolution in only minimal amounts of water. In some instances, a small amount of silicified microcrystalline cellulose—generally less than about 10 weight percent of the pharmaceutical formulation—may also be incorporated into the formulation to further aid dissolution in water. The use silicified microcrystalline cellulose is not required, however, and in some instances, the tablet may be formulated with no silicified microcrystalline cellulose at all.

In addition to being rapidly soluble in only a minimal amount of water, the tablet of the present disclosure also advantageously has been found to provide improved stability or shelf life for the active ingredients used in the formulation, particularly the second active ingredient. Such stability may be tested under different conditions.

For instance, the pharmaceutical formulation may be stored for a relatively short time of 7 days at a very high storage temperature of about 60 degrees C. In certain embodiments of the present disclosure, at least 85 percent by weight of the second active ingredient remains present in the pharmaceutical formulation after being stored under such harsh conditions.

Alternatively, the pharmaceutical formulation may be stored for a longer time of 30 days under somewhat milder storage conditions of a temperature of 40 degrees C. and a relative humidity of about 75%. In certain embodiments of the present disclosure, at least 95 percent by weight of the second active ingredient remains present in the pharmaceutical formulation after being stored under such conditions.

Further still, the pharmaceutical formulation may be stored for up to 90 days under somewhat storage conditions of a temperature of 25 degrees C. and a relative humidity of about 60% which simulate typical room temperature storage conditions. In certain embodiments of the present disclosure, at least 98 percent by weight of the second active ingredient remains present in the pharmaceutical formulation after being stored under such conditions.

The quick dissolving pharmaceutical tablet may in general be prepared by blending all of the aforementioned components to form a mixture and then compressing the mixture into a final tablet shape.

In general, the crospovidone is preferably dried to a moisture content below 0.5 weight percent prior to mixing. If silicified microcrystalline cellulose is included as an excipient in the mixture, then the silicified microcrystalline cellulose is also preferably dried to a moisture content below 0.5 weight percent prior to mixing.

It is also preferred to first mix the first and second active ingredients, mannitol, crospovidone, colloidal silicon dioxide, silicified microcrystalline cellulose (if any), and any other excipients except for sodium stearyl fumarate to form an intermediate mixture. After these components are blended and sieved, this intermediate mixture may then be combined with the sodium stearyl fumarate to form a final mixture. The final mixture may in turn then be compressed into tablets.

In an additional aspect, the present disclosure provides a method of treating a bacterial infection. According to one embodiment, the method includes administering an effective amount of a pharmaceutical formulation to a patient in need of such treatment. The pharmaceutical formulation includes at least the following components: (1) from about 35 to about 50 weight percent a first active ingredient which comprises amoxicillin or a pharmaceutically acceptable salt thereof; (2) from about 2.0 to about 12 weight percent a second active ingredient which comprises clavulanic acid or a pharmaceutically acceptable salt thereof; (3) from about 30 to about 40 weight percent mannitol; (4) from about 2 to about 7 weight percent crospovidone; (5) from about 0.5 to about 2.0 weight percent colloidal silicon dioxide; and (6) from about 2.0 to about 5.0 weight percent sodium stearyl fumarate. The pharmaceutical formulation is preferably administered in the form of a tablet, and more particularly in the form of a tablet which rapidly solubilized in only a minimal amount of water, typically 5 milliliters of water or less.

The following non-limiting examples illustrate various additional aspects of the disclosure. Unless otherwise indicated, percentages are by weight based on the overall weight of the composition.

EXAMPLE 1

Effect of Excipients on Active Ingredient Stability

In this set of tests, the stability of two active ingredients—amoxicillin trihydrate and potassium clavulanate—was studied under stressed storage conditions (temperature of about 60° C. for about 7 days). In particular, the effect of different excipients and different mixture preparation conditions on the stability of the active ingredients was analyzed.

Samples of substantially pure potassium clavulanate and amoxicillin trihydrate—without excipients—were stored at about 60° C. for about 7 days and then assayed to serve as controls.

In addition, two sets of compatibility studies with various excipients were conducted to investigate the influence of excipients on the stability of clavulanic acid and amoxicillin in the final dosage form. In the first study, a total of eight binary (i.e. two component) mixtures were prepared, each combining: (1) either amoxicillin trihydrate or potassium clavulanate; and (2) one of the following excipients: (a) silicified microcrystalline cellulose, (b) low moisture silicified microcrystalline cellulose, having a moisture content of less than about 3.0%, (c) crospovidone, or (d) mannitol. In the first study, each of the binary mixtures of amoxicillin trihydrate/potassium clavulanate and excipients was prepared with non-dried excipient materials at a normal relative humidity (RH) of about 45-65%. After storage at a temperature of about 60° C. for about 7 days, each of the mixtures was then assayed to determine the amount of active ingredient remaining.

Similarly, in the second study, a total of eight binary mixtures were prepared, each combining: (1) either amoxicillin trihydrate or potassium clavulanate; and (2) one of the following excipients: (a) silicified microcrystalline cellulose, (b) low moisture silicified microcrystalline cellulose, (c) crospovidone, or (d) colloidal silicon dioxide. In the second study, however, the excipient for each of the binary mixtures was pre-dried to a moisture content of less than about 0.5% prior to combining with the amoxicillin trihydrate or potassium clavulanate. Further, each of the binary mixtures in the second study was prepared in a reduced moisture environment at a normal relative humidity (RH) of less than 30%. After storage at a temperature of about 60° C. for about 7 days, each of the mixtures was then assayed to determine the amount of active ingredient remaining. The assay results are shown in the following Tables 1 & 2:

TABLE 1

Assay Of Amoxicillin After Storage For 7 Days At 60° C.

| Sample | Assay of amoxicillin (%) | Remarks |
|---|---|---|
| Amoxicillin (AMX) | 99 | Control Sample |
| AMX + Prosolv SMCC50 | 102 | A) non-dried material |
| AMX + Prosolv SMCC50 LM | 101 | B) preparation conditions: |
| AMX + Crospovidone | 98 | 45-65% Relative Humidity |
| AMX + Mannitol | 96 | |
| AMX + Prosolv 90 dry | 100 | A) pre-dried material |

TABLE 1-continued

Assay Of Amoxicillin After Storage For 7 Days At 60° C.

| Sample | Assay of amoxicillin (%) | Remarks |
|---|---|---|
| AMX + Prosolv SMCC50 dry | 111 | B) preparation conditions: |
| AMX + Crospovidone dry | 103 | <30% Relative Humidity |
| AMX + Syloid dry | 90 | |

TABLE 2

Assay Of Clavulanic Acid After Storage For 7 Days At 60° C.

| Sample | Assay of clavulanic acid (%) | Remarks |
|---|---|---|
| Clavulanic acid (CA) | 94 | Control Sample |
| CA + Prosolv SMCC50 | 13 | A) non-dried material |
| CA + Prosolv SMCC50 LM | 0 | B) preparation conditions: |
| CA + Crospovidone | 77 | 45-65% Relative Humidity |
| CA + Mannitol | 92 | |
| CA + Prosolv 90 dry | 94 | A) pre-dried material |
| CA + Prosolv SMCC50 dry | 89 | B) preparation conditions: |
| CA + Crospovidone dry | 98 | <30% Relative Humidity |
| CA + Syloid dry | 98 | |

These assay results demonstrate that amoxicillin is compatible with all tested excipients irrespective of the preparation conditions (non-dry material and normal humidity vs. pre-dried material and low humidity).

With potassium clavulanate, however, differences in these preparation conditions were observed to significantly affect the storage stability of the clavulanate. In the first study, with excipients which had not been pre-dried, a significant decrease in assay of potassium clavulanate was observed for the majority of the binary mixtures. Most notably, the clavulanate completely degraded in the presence of silicified microcrystalline cellulose (Prosolv SMCC). When pre-dried excipient materials and dry mixing conditions were utilized in the second study, however, the decrease in the assay of the clavulanate was observed to be much less. This indicates that the clavulanate active ingredient is more stabile when the excipients are pre-dried. This is especially the case for excipients which are known to have a high capacity for water binding such as silicified microcrystalline cellulose and crospovidone.

EXAMPLE 2

Stability of Inventive and Comparative Tablet Formulations

In the Example, a series of three tablet formulations were prepared in accordance with the present invention. Three comparative tablet formulations were also prepared. The stability of the tablets under various storage conditions was then examined.

For each of the three inventive tablet formulations, all of the tablet components (except sodium stearyl fumarate) were blended and sieved to form an intermediate mixture. This mixture was then blended with sodium stearyl fumarate to provide a final mixture. The final mixture was then compressed in tablets of appropriate hardness by rotary tablet press. In each instance, the crospovidone excipient was dried to LOD below 0.5% before blending. The make-up of the 3 inventive tablets was as shown in Table 3:

TABLE 3

Inventive Tablet Compositions:

| | Amount per tablet (mg) | | |
|---|---|---|---|
| Component | Inventive Tablet 1 | Inventive Tablet 2 | Inventive Tablet 3 |
| Amoxicillin (as trihydrate) | 600.0 | 600.0 | 600.0 |
| Clavulanic acid (as Potassium clavulanate) | 42.9 | 42.9 | 42.9 |
| Crospovidone | 30.0 | 75.0 | 40.0 |
| Colloidal Silicon Dioxide | 10.0 | 10.0 | 10.0 |
| Fruit flavour | 40.0 | 40.0 | 40.0 |
| Sucralose | 6.0 | 5.500 | 5.500 |
| Sodium Stearyl Fumarate | 60.0 | 29.0 | 29.0 |
| Silicified Microcrystalline Cellulose | 0 | 0 | 100.0 |
| Mannitol | 511.1 | 497.6 | 432.6 |
| Total mass (mg) | 1300.0 | 1300.0 | 1300.0 |

Likewise for each of the three comparative tablet formulations, all of the tablet components (except sodium stearyl fumarate) were blended and sieved to form an intermediate mixture. This mixture was then blended with sodium stearyl fumarate to provide a final mixture. The final mixture was then compressed in tablets of appropriate hardness by rotary tablet press. In each instance—except Comparative Tablet 3—the crospovidone excipient was dried to LOD below 0.5% before blending. The make-up of the 3 comparative tablets was as shown in Table 4:

TABLE 4

Comparative Tablet Compositions:

| | Amount per tablet (mg) | | |
|---|---|---|---|
| Component | Comp. Tablet 1 | Comp. Tablet 2 | Comp. Tablet 3 |
| Amoxicillin (as trihydrate) | 600.0 | 600.0 | 600.0 |
| Clavulanic acid (as Potassium clavulanate) | 42.9 | 42.9 | 42.9 |
| Crospovidone | 30.0 | 10.0 | 40.0 |
| Colloidal Silicon Dioxide | 5.0 | 10.0 | 10.0 |
| Fruit flavour | 40.0 | 40.0 | 40.0 |
| Sucralose | 6.0 | 5.5 | 5.5 |
| Sodium Stearyl Fumarate | 30.0 | 30.0 | 29.0 |
| EMDEX (dextrate binder) | 546.1 | 0 | 0 |
| Mannitol | 0 | 561.6 | 432.6 |
| Silicified Microcrystalline Cellulose | 0 | 0 | 100.0 |
| Total mass (mg) | 1300.0 | 1300.0 | 1300.0 |

As can be seen from this table, in comparative tablet 1, EMDEX dextrate binder was used in place of mannitol. In comparative tablet 2, however, an excess of mannitol (43.2%) was used while a reduced amount (0.77%) of crospovidone was used.

The stability of the clavulanic acid (as Potassium clavulanate) each of the tablet formulations was then examined under three different storage conditions. In the first set of tests, sample tablets from each of the formulations were stored for a relatively short time of 7 days at a very high storage temperature of about 60 degrees C. The tablets were then assayed to measure decrease in the amount of clavulanic acid in the tablet.

In the second set of tests, sample tablets from each of the formulations were stored stored for a longer time of 30 days under somewhat milder storage conditions of a temperature of 40 degrees C. and a relative humidity of about 75%. Theses tablets were then also assayed to measure the decrease in the amount of clavulanic acid in the tablet.

In the third set of tests, sample tablets from each of the formulations were stored stored for up to 90 days under somewhat storage conditions of a temperature of 25 degrees C. and a relative humidity of about 60% which simulate typical room temperature storage conditions. Theses tablets were also assayed to measure the decrease in the amount of clavulanic acid in the tablet. The assay results are shown in the following Table 5:

TABLE 5

Potassium Clavulanate Storage Stability Assay Results

| | Tablet Storage Conditions | | |
|---|---|---|---|
| Tablet Formulation | 7 days at 60° C. | 30 days at 40° C. and RH 75% | 90 days at 25° C. and RH 60% |
| | Percent Decrease in Clavulanate Assay | | |
| Inventive 1 | 9.9% | 4.3% | 0.0% |
| Inventive 2 | 11.5% | 1.6% | 1.2% |
| Inventive 3 | 11.0% | 0.5% | n.a. |
| Comparative 1 | complete decomposition of formulation | n.a. | n.a. |
| Comparative 2 | 35.0% | 7.6% | n.a. |
| Comparative 3 | 17.1% | n.a. | n.a. | n.a.—data not available

These results clearly demonstrate that pharmaceutical tablet formulations prepared in accordance with the present disclosure exhibit superior long term stability compared to other tablet formulations prepared using different combinations of excipients.

EXAMPLE 3

Comparison of Inventive Tablet Storage Stability to Oral Suspensions

In this Example, the storage stability of clavulanic acid in quick dissolving tablets prepared according to the current disclosure was compared to that of commercially available oral suspensions of amoxicillin and clavulanic acid.

For the test, three different tablet formulations were prepared in accordance with the present disclosure and stored Al-Al blister packaging. The formulations were the same as those described for Inventive Tablets 1-3 in Example 2. For each of the three tablet formulations, one set of tablets was stored for about 10 days at about 25 degrees C. and about 60% relative humidity. A second set of tables from each of the three formulations was stored for about 10 days at about 40 degrees C. and about 75% relative humidity.

For comparative purposes, four reconstituted oral suspensions of amoxicillin and clavulanic acid were prepared according to the user instructions and stored under refrigeration in the original packaging in HDPE bottles at a temperature of about 5 degrees C. for about 10 days.

After 10 days, all of the samples were analyzed for assay of amoxicillin and clavulanic acid to determine the loss of active ingredients due to decomposition during storage. No significant changes in amoxicillin were observed. For the clavulanic acid, the results are shown in the following Table 6:

TABLE 6

Decrease In Assay Of Clavulanic Acid (CA) After 10 Day Storage:

| Sample | Decrease in assay of clavulanic acid (%) | Storage Conditions |
|---|---|---|
| Oral Suspension 1 | 14.9 | 5° C. |
| Oral Suspension 2 | 17.0 | (refrigerated) |
| Oral Suspension 3 | 17.3 | |
| Oral Suspension 4 | 17.6 | |
| Inventive Tablet Formulation 1 | 0.2 | 25° C. & 60% Relative Humidity |
| Inventive Tablet Formulation 2 | 0.1 | |
| Inventive Tablet Formulation 3 | 0.6 | |
| Inventive Tablet Formulation 1 | 0.0 | 40° C. & 75% Relative Humidity |
| Inventive Tablet Formulation 2 | 0.2 | |
| Inventive Tablet Formulation 3 | 1.4 | |

As can be seen from this table, the inventive tablet formulations were found to exhibit superior stability (i.e. less degradation of the clavulanic acid active ingredient) as compared to the oral suspension. No significant decrease in assay of clavulanic acid was observed for the inventive table formulations when stored at either at 25° C./RH 60% or 40° C./RH 75%. On the other hand, for the comparative oral suspensions, a high decrease in assay of clavulanic acid (15-18%) over the period of 10 days was observed when stored even under refrigerated conditions.

Moreover, it should be noted that during evaluation, the reconstituted suspensions were taken out of the refrigerator for a maximum of only five times for sampling over the 10 day period. However, in the real-life situations the patient must take the suspension out of the refrigerator at least 20 times during the treatment (twice a day for 10 days). Therefore, the degradation and loss of clavulanic acid would be even more pronounced under real world conditions.

In contrast to the reconstituted oral suspension, however, the inventive formulation is stable even at elevated temperatures, allowing excursions up to 40° C., which makes it convenient also for travel usage.

The previously described embodiments of the present disclosure have many advantages. The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention.

What is claimed is:

1. A quick dissolving pharmaceutical formulation comprising:
   from about 35 to about 50 weight percent of a first active ingredient which comprises amoxicillin or a pharmaceutically acceptable salt thereof;
   from about 2.0 to about 12 weight percent of a second active ingredient which comprises clavulanic acid or a pharmaceutically acceptable salt thereof;
   from about 30 to about 40 weight percent mannitol;
   from about 2 to about 7 weight percent crospovidone;
   from about 0.5 to about 2.0 weight percent colloidal silicon dioxide;
   from about 2.0 to about 5.0 weight percent sodium stearyl fumerate; and
   silicified microcrystalline cellulose in an amount less than about 10 weight percent of the pharmaceutical formulation.

2. The pharmaceutical formulation of claim 1, wherein the formulation further comprises from about 5.0 to about 10 weight percent silicified microcrystalline cellulose.

3. The pharmaceutical formulation of claim 1, wherein the first active ingredient comprises amoxicillin trihydrate.

4. The pharmaceutical formulation of claim 1, wherein the second active ingredient comprises potassium clavulanate.

5. The pharmaceutical formulation of claim 1, wherein the ratio of the first active ingredient to the second active ingredient in the formulation, on a weight basis, is from about 4:1 to about 14:1.

6. The pharmaceutical formulation of claim 1, wherein the pharmaceutical formulation is a tablet comprising from about 125 to about 600 mg of the first active ingredient.

7. The pharmaceutical formulation of claim 1, wherein the pharmaceutical formulation is a tablet capable of being solubilized in water.

8. The pharmaceutical formulation of claim 1, wherein the pharmaceutical formulation is a tablet capable of being solubilized in 5 milliliters of water.

9. The pharmaceutical formulation of claim 1, wherein the crospovidone is pre-dried to a moisture content below 0.5 weight percent before being incorporated into the pharmaceutical formulation.

10. The pharmaceutical formulation of claim 1, wherein the silicified microcrystalline cellulose is pre-dried to a moisture content below 0.5 weight percent before being incorporated into the pharmaceutical formulation.

11. The pharmaceutical formulation of claim 1, wherein at least 88 percent by weight of the second active ingredient remains present in the pharmaceutical formulation after being stored for 7 days at a temperature of 60 degrees C.

12. The pharmaceutical formulation of claim 1, wherein at least 95 percent by weight of the second active ingredient remains present in the pharmaceutical formulation after being stored for 30 days at a temperature of 40 degrees C. and a relative humidity of about 75%.

13. The pharmaceutical formulation of claim 1, wherein at least 98 percent by weight of the second active ingredient f remains present in the pharmaceutical formulation after being stored for 90 days at a temperature of 25 degrees C. and a relative humidity of about 60%.

14. A method of treating a bacterial infection comprising administering an effective amount of the pharmaceutical formulation of claim 1 to a patient in need of such treatment.

15. A method for making a quick dissolving pharmaceutical tablet, comprising the steps of:
   pre-drying crospovidone to a moisture content below 0.5 weight percent;
   blending (i) a first active ingredient which comprises amoxicillin or a pharmaceutically acceptable salt thereof, (ii) a second active ingredient which comprises clavulanic acid or a pharmaceutically acceptable salt thereof, (iii) mannitol, (iv) crospovidone, and (v) colloidal silicon dioxide to form an intermediate mixture;
   further blending sodium stearyl fumerate to form a final mixture; and
   compressing the final mixture into pharmaceutical tablets.

16. The method of claim 15, further comprising the step of pre-drying silicified microcrystalline cellulose to a moisture content below 0.5 weight percent and wherein the pre-dried silicified microcrystalline cellulose is blended into the intermediate mixture.

17. The method of claim 15, wherein the first active ingredient comprises amoxicillin trihydrate.

18. The method of claim 15, wherein the second active ingredient comprises potassium clavulanate.

19. The method of claim 15, wherein the tablet is capable of being solubilized in water.

20. The method of claim 15, wherein the tablet is capable of being solubilized in 5 milliliters of water.

* * * * *